(12) United States Patent  (10) Patent No.: US 7,872,884 B2
Parramon et al.  (45) Date of Patent: Jan. 18, 2011

(54) CASCADED STEP-UP CONVERTER AND CHARGE PUMP FOR EFFICIENT COMPLIANCE VOLTAGE GENERATION IN AN IMPLANTABLE STIMULATOR DEVICE

(75) Inventors: Jordi Parramon, Valencia, CA (US); Goran N. Marnfeldt, Hollviken (SE)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 511 days.

(21) Appl. No.: 11/266,646

(22) Filed: Nov. 3, 2005

(65) Prior Publication Data

US 2007/0097719 A1    May 3, 2007

(51) Int. Cl.
*H02M 3/18*    (2006.01)
*G05F 1/40*    (2006.01)
(52) U.S. Cl. ........................................ 363/60; 323/265
(58) Field of Classification Search ................. 323/265, 323/273, 312, 313; 363/56, 60
See application file for complete search history.

(56) References Cited

U.S. PATENT DOCUMENTS

| | | | | |
|---|---|---|---|---|
| 4,050,004 | A | 9/1977 | Greatbatch | 363/59 |
| 4,134,408 | A | 1/1979 | Brownlee | 607/33 |
| 5,193,539 | A | 3/1993 | Schulman et al. | 607/61 |
| 5,193,540 | A | 3/1993 | Schulman et al. | 607/61 |
| 5,312,439 | A | 5/1994 | Loeb | 607/2 |
| 5,405,367 | A | 4/1995 | Schulman et al. | 607/61 |
| 5,433,737 | A | 7/1995 | Aimone | 607/72 |
| 5,723,969 | A | 3/1998 | Archer | 607/5 |
| 5,836,981 | A | 11/1998 | Chang | 607/9 |
| 6,035,235 | A | 3/2000 | Perttu | 607/5 |
| 6,035,237 | A | 3/2000 | Schulman | 607/63 |
| 6,051,017 | A | 4/2000 | Loeb et al. | 607/1 |
| 6,061,596 | A | 5/2000 | Richmond et al. | 607/41 |
| 6,164,284 | A | 12/2000 | Schulman et al. | 128/899 |
| 6,175,764 | B1 | 1/2001 | Loeb et al. | 607/3 |
| 6,181,965 | B1 | 1/2001 | Loeb et al. | 607/3 |
| 6,185,452 | B1 | 2/2001 | Schulman et al. | 604/20 |

(Continued)

OTHER PUBLICATIONS

U.S. Appl. No. 11/177,503, filed Jul. 8, 2005, Peterson et al.

(Continued)

*Primary Examiner*—Adolf Berhane
(74) *Attorney, Agent, or Firm*—Wong, Cabello, Lutsch, Rutherford & Brucculeri, LLP (57) ABSTRACT

Disclosed herein are circuits and methods for generating a compliance voltage from a battery voltage in an implantable stimulator device. In one embodiment, the battery voltage is boosted to form the compliance voltage for driving the current sources (DACs) that provide therapeutic current to the electrodes on the device. Such improved boosting circuitry is preferably cascaded and comprises two stages. The first stage is preferably a step-up converter, which is used to generate an intermediate voltage from the battery voltage. The second stage is preferably a charge pump, which is used to generate the compliance voltage from the intermediate voltage. By splitting the boosting into stages, power efficiency during generation of high voltages is improved compared to the use of step-up converters and resolution in setting the compliance voltage is improved compared to the use of charge pumps alone. Moreover, depending on the compliance voltage to be produced by the boosting circuitry, the various stages can be selectively activated.

29 Claims, 7 Drawing Sheets

U.S. PATENT DOCUMENTS

| | | | |
|---|---|---|---|
| 6,185,455 B1 | 2/2001 | Loeb et al. | 607/3 |
| 6,208,894 B1 | 3/2001 | Schulman et al. | 607/2 |
| 6,208,896 B1 | 3/2001 | Mulhauser | 607/5 |
| 6,214,032 B1 | 4/2001 | Loeb et al. | 607/1 |
| 6,289,246 B1 | 9/2001 | Money | 607/56 |
| 6,315,721 B2 | 11/2001 | Schulman et al. | 600/301 |
| 6,324,426 B1 | 11/2001 | Thompson | 607/16 |
| 6,392,580 B1 | 5/2002 | Swanson | 341/155 |
| 6,516,227 B1 | 2/2003 | Meadows et al. | 607/46 |
| 6,525,949 B1 * | 2/2003 | Johnson et al. | 363/60 |
| 6,745,077 B1 | 6/2004 | Griffith et al. | 607/61 |
| 6,756,772 B2 * | 6/2004 | McGinnis | 323/225 |
| 6,856,838 B2 | 2/2005 | Parramon et al. | 607/61 |
| 6,871,090 B1 | 3/2005 | He et al. | 607/2 |
| 6,909,915 B2 | 6/2005 | Greatbatch | 607/5 |
| 6,934,584 B1 | 8/2005 | Wong | 607/9 |
| 7,304,871 B2 * | 12/2007 | Ito et al. | 363/59 |
| 7,307,385 B2 * | 12/2007 | Yamamoto et al. | 315/224 |
| 2004/0059392 A1 | 3/2004 | Parramon et al. | 607/36 |
| 2004/0183607 A1 | 9/2004 | Moore | 331/117 |
| 2005/0021108 A1 | 1/2005 | Klosterman et al. | 607/48 |
| 2005/0057905 A1 | 3/2005 | He et al. | 361/760 |
| 2005/0270812 A1 * | 12/2005 | Vinciarelli | 363/65 |

OTHER PUBLICATIONS

U.S. Appl. No. 11/138,632, filed May 26, 2005, Parramon et al.

Document # IPCOM000016848D, published at www.ip.com (Jul. 18, 2003).

Document # IPCOM000007552D, published at www.ip.com (Apr. 4, 2002).

* cited by examiner

V+ level detector and logic 350:

- If V+ ≤ Vbat, then X=0 and Y=0     all conversion stages bypassed

- If Vbat < V+ < 7.5V, then X=1 and Y=0     charge pump stage 295 bypassed; only step up stage 290 active

- If V+ ≥ 7.5V, then X=1 and Y=1     both conversion stages active

*Figure 7*

CASCADED STEP-UP CONVERTER AND CHARGE PUMP FOR EFFICIENT COMPLIANCE VOLTAGE GENERATION IN AN IMPLANTABLE STIMULATOR DEVICE

FIELD OF THE INVENTION

The present invention relates generally to implantable stimulator devices, e.g., an implantable pulse generator such as a Bion® device, a Spinal Cord Stimulation (SCS) device, or other type of neural stimulation devices. More particularly, the present invention relates to DC-to-DC conversion circuitry capable of increasing a battery voltage to a higher compliance voltage used to generate the therapeutic pulses in the device.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a Bion® device (Bion® is a registered trademark of Advanced Bionics Corporation, of Valencia, Calif.), such as that disclosed in U.S. Published Patent Applications 2005/0021108, published Jan. 27, 2005, 2005/0057905, published Mar. 17, 2005, and 2004/0059392, published Mar. 25, 2004, which are all incorporated herein by reference in their entireties. However, the present invention also has applicability in other implantable stimulator devices, such as Spinal Cord Stimulation (SCS) devices, an example of which can be found in U.S. Pat. No. 6,516,227, which is incorporated herein by reference in its entirety Bion® devices are typically characterized by a small, cylindrical housing that contains electronic circuitry that produces the desired electric stimulation current between spaced electrodes. These devices, also referred to as microstimulators, are implanted proximate to the target tissue so that the stimulation current produced by the electrodes stimulates the target tissue to reduce symptoms or otherwise provide therapy for a wide variety of conditions and disorders. Further examples of microstimulators can be found in the following disclosures, which are all incorporated by reference in their entireties: U.S. Pat. Nos. 5,312,439; 5,193,539; 5,193,540; 5,405,367; 6,185,452; 6,315,721; 6,061,596; 6,051,017; 6,175,764; 6,181,965; 6,185,455; 6,214,032; 6,164,284; 6,208,894.

Figure 1:
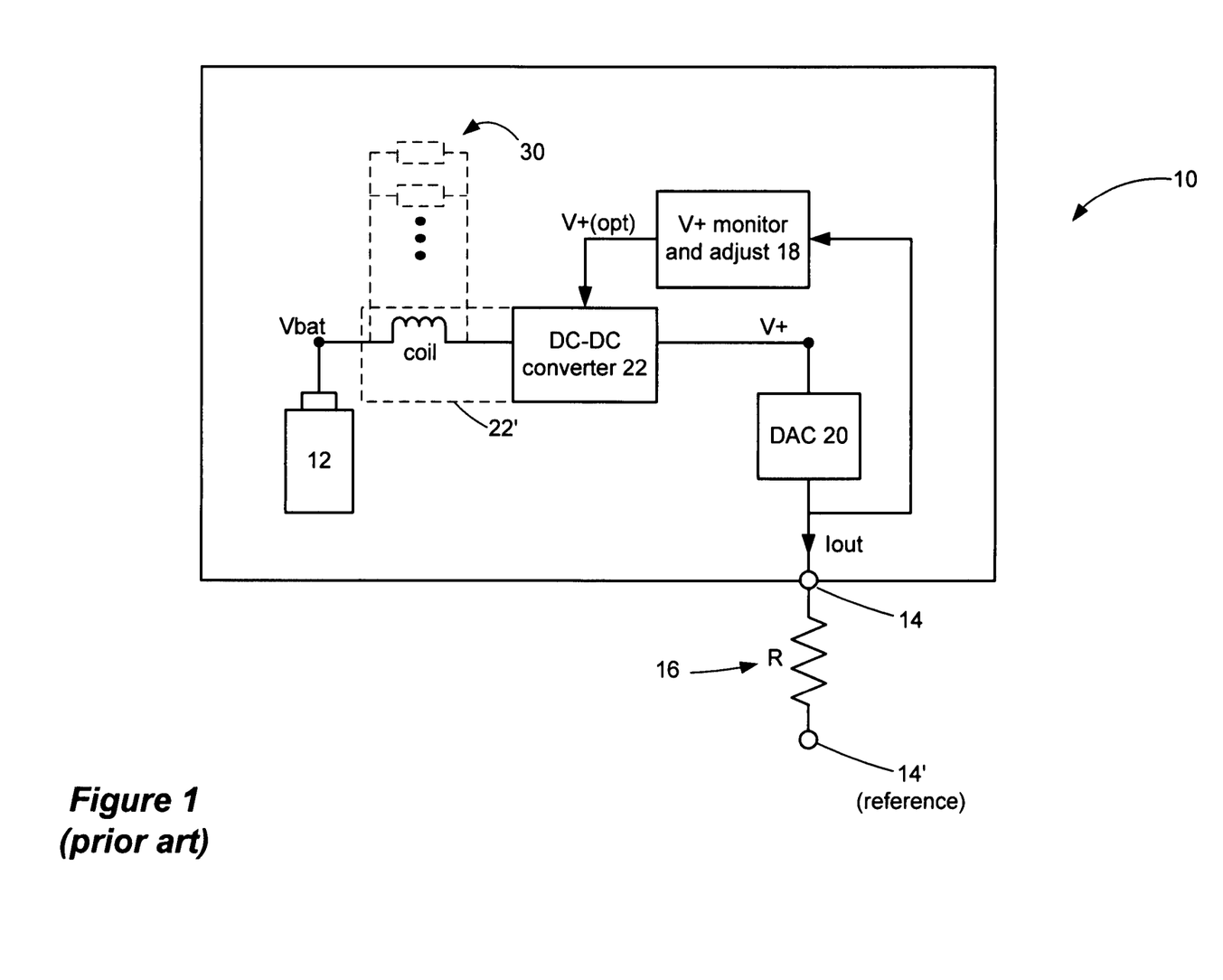
FIG. 1 illustrates DC-to-DC converter circuitry and a feedback loop for creating a compliance voltage from a battery voltage in an implantable pulse generator (IPG) in accordance with the prior art.

As is known, and as shown in FIG. 1, an implantable stimulator device 10 generally comprises a battery 12. The battery 12, which may or may not be rechargeable, generally provides power to the internal logic circuitry of the device 10 (not shown). Importantly, the battery 12 also provides the power necessary to send a therapeutic stimulating current through the stimulating electrode(s) 14 on the device, so that such current is directed to tissue 16 to be treated. In this regard, the device 10 is generally programmed to provide a constant current pulse (Iout) to the tissue 16. The current is ultimately provided by a current source 20 coupled to the electrode 14, and because such a current source is generally digitally programmable to provide a precise amount of current, such a current source is generally referred to as a Digital-to-Analog Converter, or "DAC" 20. Ultimately, the current provided to the tissue 16 is set with respect to a reference potential (usually ground) as designated generically by node 14', which may comprise another electrode on the device 10 (and which may or may not be coupled to a DAC of its own), the case of the device 10, or some other potential.

For the DAC 20 to be able to provide the programmed output current, Iout, the DAC 20 must receive a power supply voltage, which is typically called the compliance voltage, V+, and which is generated via a DC-to-DC converter circuit 22. This generated compliance voltage V+ is variable, and its optimal value, V+(opt), depends on the magnitude of the programmed stimulation current, the resistance of the tissue 16, and other factors. Determination of the optimal compliance voltage V+(opt) is accomplished by a compliance voltage monitoring and adjust circuit 18. The details of compliance voltage monitoring and adjust circuit 18 are not directly germane to this disclosure, but in any event further details concerning such circuitry in an implantable stimulator device 10 can be found in the following documents published at www.ip.com, which are both incorporated herein by reference: #IPCOM000016848D, published Jul. 18, 2003, #IPCOM000007552D, published Apr. 4, 2002. Basically, if V+ is too low, the DAC 20 will become "loaded" and unable to provide the desired current, Iout. If V+ is too high, the DAC 20 will be able to provide the desired current, Iout, but power will be wasted: i.e., some portion of the compliance voltage V+ will be dropped across the DAC 20 without any useful effect. Therefore, the basic purpose of compliance voltage monitoring and adjust circuit 18 is to deduce V+(opt) so that V+ is not to high or too low.

In any event, DC-to-DC converter circuitry 22, which is the focus of this disclosure, receives this deduced optimal compliance voltage V+(opt), and attempts to match the actual compliance voltage V+ it produces to that value. The basic function of the converter circuitry 22 is to boost the voltage, Vbat, provided by the battery 12 in the device 10 to produce a higher compliance voltage V+ matching V+(opt). To provide some exemplary numbers, Vbat might constitute between 3 to 5 Volts, from which the converter circuitry 22 generates a compliance voltage V+ of up to 18 Volts.

In the prior art, DC-to-DC converter circuitry 22 generally comprises two different types of circuits: step-up converters and charge pumps. As is known, a step-up converter utilizes a switched LC circuit to charge a coil, and then forces the charge on the coil to a capacitor. (The operation of a step-up converter will be explained in more detail later). Such step-up converters can achieve high voltages required for the compliance voltage in an implantable stimulator device application, but suffer from drawbacks. First, the efficiency of step-up converters becomes increasingly worse as higher compliance voltages are called for. Specifically, discharge of the capacitor on the switch is particularly lossy when high voltages are being generated. Such power loss at high voltages is of particular concern in implantable stimulator devices, because, as noted, such devices are normally powered by batteries 12; if power is needlessly wasted, the device 10 could fail sooner, or might require more frequent recharging, thus inconveniencing the patient in which the device is implanted.

Another drawback to the use of step-up converters involves the necessity of the charging coil. Because implantable stimulator devices are generally small, and space within the device is at a premium, it is generally advantageous to use the coil in the step-up converter for other purposes, such as for receiving EM/RF energy for externally charging the battery or for receiving and sending data telemetry between the device and an external components. However, if a single coil is used for these functions and as the coil in the step-up converter, the step up converter may place high voltages across the coil. Other circuits 30 also using the coil for other functions may have difficulty handling such high voltages, and would need to be selectively isolated or risk being damaged. In short, use of a step-up converter for converter 22 has limitations in an implantable stimulator device application, particularly when high compliance voltages are required.

Another circuit useable as a DC-to-DC converter 22 in an implantable stimulator device 10 is a charge pump. As is known, and as will be explained in further detail later this disclosure, a charge pump employs a capacitor whose top and bottom plates are selectively charged in an alternating fashion by a series of clocking signals, with the effect of boosting the input voltage to a higher DC value. Charge pumps are generally very efficient when compared to step-up converters. However, it is generally more difficult to tailor the output voltage of a charge pump to a precise value, which hampers its utility in an implantable stimulator device application, which requires sensitive and precise compliance voltage adjustment. To address this implementation drawback, a large number of additional capacitors could be used in conjunction with the charge pump, but such additional capacitors would likely need to be "off chip," i.e., off the integrated circuit on which the current sources and other logic circuitry are formed. Using additional off-chip capacitors adds to the complexity of the device, and requires additional space, which as just noted is a significant constraint in an implantable device.

Accordingly, the implantable stimulator art would benefit from improved DC-to-DC converter circuitry for adjustably boosting the battery voltage to the compliance voltage needed to provide power to the stimulating electrode(s). Embodiments of such a solution are provided herein.

SUMMARY

Disclosed herein are circuits and methods for generating a compliance voltage from a battery voltage in an implantable stimulator device. In one embodiment, the battery voltage is boosted to form the compliance voltage for driving the current sources (DACs) that provide therapeutic current to the electrodes on the device. Such improved boosting circuitry is preferably cascaded and comprises two stages. The first stage is preferably a step-up converter, which is used to generate an intermediate voltage from the battery voltage. The second stage is preferably a charge pump, which is used to generate the compliance voltage from the intermediate voltage. By splitting the boosting into stages, power efficiency during generation of high voltages is improved compared to the use of step-up converters alone and resolution in setting the compliance voltage is improved compared to the use of charge pumps alone. Moreover, depending on the compliance voltage to be produced by the boosting circuitry, the various stages can be selectively activated.

BRIEF DESCRIPTION OF THE DRAWINGS

The above and other aspects of the present invention will be more apparent from the following more particular description thereof, presented in conjunction with the following drawings wherein.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims and their equivalents.

Before discussing the DC-to-DC converter circuitry which is a central aspect of this disclosure, the circuitry, structure, and function of an implantable stimulator device in which the circuitry can be used is set forth for completeness. As noted earlier, the disclosed implantable stimulator device may comprise a Bion® device, an SCS device, or similar electrical stimulator and/or electrical sensor. However, for convenience, the inventive circuitry is disclosed herein in the context of a Bion® device, referred to generically herein as an implantable pulse generator (IPG). However, it is to be understood that the invention is not so limited. Rather, the invention may be used with any type of implantable electrical circuitry that could benefit from improved voltage boosting. For example, the present invention may be used as part of a pacemaker, an implantable pump, a defibrillator, a cochlear stimulator, a retinal stimulator, a stimulator configured to produce coordinated limb movement, a cortical or deep brain stimulator, or in any other stimulator configured to treat urinary incontinence, sleep apnea, shoulder sublaxation, etc. Moreover, the technique can be used in non-medical and/or non-implantable devices or systems as well.

Figure 2:
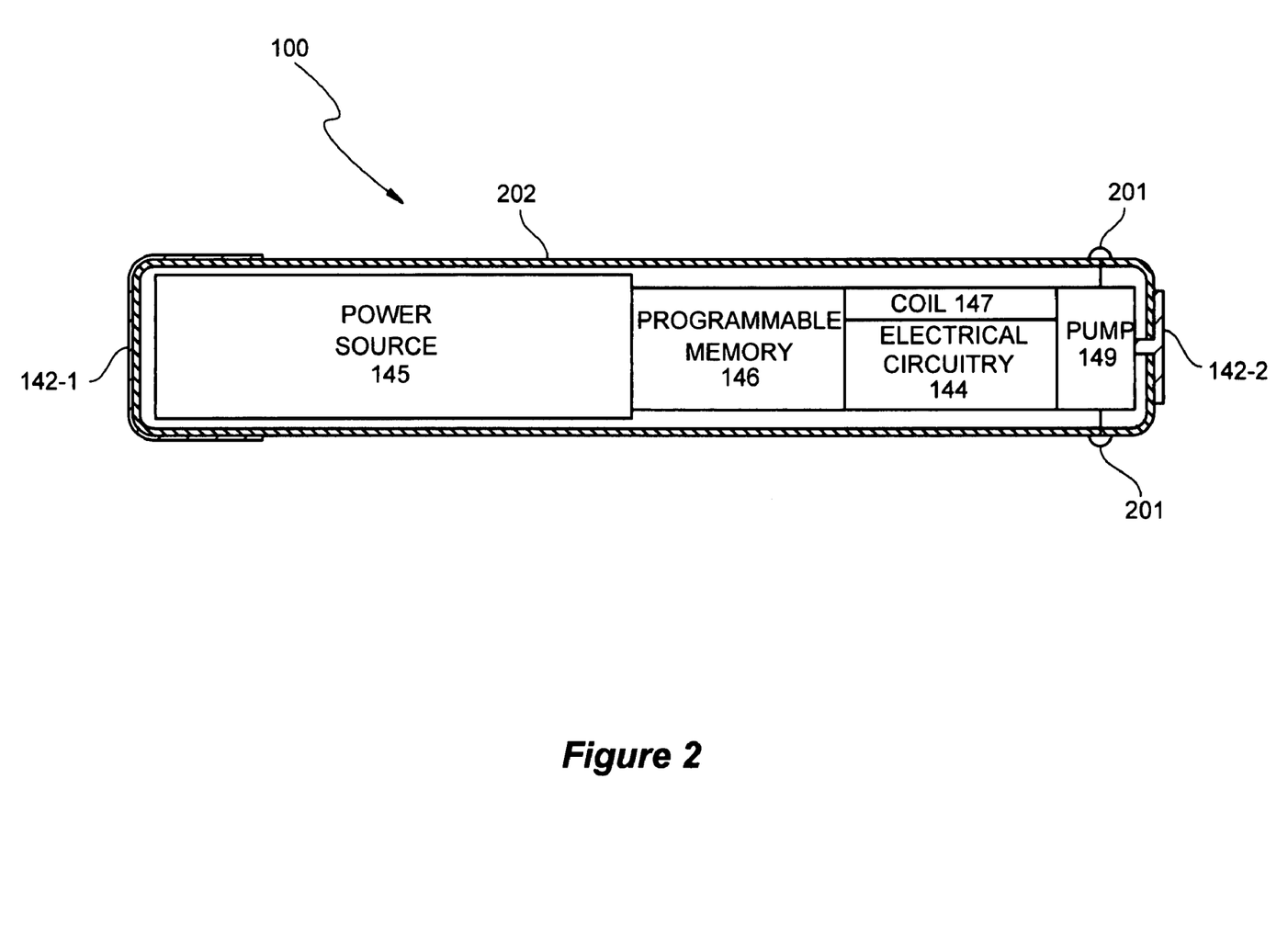
FIG. 2 illustrates an exemplary IPG in which the improved DC-to-DC converter circuitry can be used.

FIG. 2 illustrates an exemplary implantable IPG 100. As shown, the IPG 100 may include a power source 145 such as a battery, a programmable memory 146, electrical circuitry 144, and a coil 147. These components are housed within a capsule 202, preferably a thin, elongated cylinder or any other shape as best serves a particular application. The shape of the capsule 202 may be determined by the structure of the desired target tissue, the surrounding area, the method of implantation, the size and location of the power source 145 and/or the number and arrangement of external electrodes 142. In some embodiments, the volume of the capsule 202 is substantially equal to or less than three cubic centimeters.

The power source 145, e.g., battery 12 of FIG. 1, is configured to output a voltage used to supply the various components within the IPG 100 with power. The power source 145 also provides power for any stimulation current applied with the IPG 100 to nearby tissue, as discussed in the Background section of this disclosure. The power source 145 may be a primary battery, a rechargeable battery, a capacitor, or any other suitable power source. Systems and methods for recharging the power source 145, where the source 145 is rechargeable, will be described below.

The coil 147 is configured to receive and/or emit a magnetic field (also referred to as a radio frequency (RF) field) that is used to communicate with or receive power from one or more external devices that support the implanted IPG 100, examples of which will be described below. Such communication and/or power transfer may include, but is not limited to, transcutaneously receiving data from the external device, transmitting data to the external device, and/or receiving power used to recharge the power source 145.

The programmable memory unit 146 is used for storing one or more sets of data, for example, electrical stimulation parameters as described further below. The programmable memory 146 allows a patient, clinician, or other user of the IPG 100 to adjust the stimulation parameters such that the electrical stimulation is at levels that are safe and efficacious for a particular medical condition and/or for a particular patient. Electrical stimulation parameters may be controlled independently. The programmable memory 146 may be any type of memory unit such as, but not limited to, random access memory (RAM), static RAM (SRAM), EEPROM, a hard drive, or the like.

The electrical stimulation parameters may control various parameters of the stimulation current applied to a target tissue including, but not limited to, the frequency, pulse width, amplitude, burst pattern (e.g., burst on time and burst off time), duty cycle or burst repeat interval, ramp on time and ramp off time of the stimulation current, etc. To determine the strength and/or duration of electrical stimulation required to most effectively treat a particular medical condition, various indicators of the medical condition and/or a patient's response to treatment may be sensed or measured. These indicators include, but are not limited to, muscle or limb activity (e.g., electromyography (EMG)), electrical activity of the brain (e.g., EEG), neurotransmitter levels, hormone levels, and/or medication levels. In some embodiments, the IPG 100 may be configured to change the stimulation parameters in a closed loop manner in response to these measurements. The IPG 100 may be configured to perform the measurements. Alternatively, other sensing devices may be configured to perform the measurements and transmit the measured values to the IPG 100.

Specific electrical stimulation may have different effects on different types of medical conditions. Thus, in some embodiments, the electrical stimulation may be adjusted by the patient, a clinician, or other user of the IPG 100 as best serves a particular medical condition. For example, the amplitude of the stimulus current applied to a target nerve may be adjusted to have a relatively low value to target relatively large diameter fibers of the target nerve. The IPG 100 may also increase excitement of a target nerve by applying a stimulation current having a relatively low frequency to the target nerve (e.g., less than 100 Hz). The IPG 100 may also decrease excitement of a target nerve by applying a relatively high frequency to the target nerve (e.g., greater than 100 Hz). The IPG 100 may also be programmed to apply the stimulation current to a target nerve intermittently or continuously.

The IPG 100 includes electrodes 142-1 and 142-2 (akin to electrode 14 of FIG. 1) on the exterior of the capsule 200. The electrodes 142 may be disposed at either end of the capsule 202, as illustrated in FIG. 2, or placed along the length of the capsule. There may also be more than two electrodes arranged in an array. One of the electrodes 142 may be designated as a stimulating electrode to be placed close to the target tissue or treatment site and one of the electrodes 142 may be designated as an indifferent electrode (reference node) used to complete a stimulation circuit (akin to electrode 14' of FIG. 1).

The electrical circuitry 144 is configured to produce electrical stimulation pulses that are delivered to the target nerve via the electrodes 142. In some embodiments, the IPG 100 may be configured to produce monopolar stimulation, which may be achieved, for example, using the stimulator case 202 as an indifferent electrode. The IPG 100 may alternatively or additionally be configured to produce bipolar stimulation, which may be achieved, for example, using one of the electrodes of the electrode array as an indifferent electrode, as is a common practice in SCS devices.

The electrical circuitry 144 may include one or more microprocessors or microcontrollers configured to decode stimulation parameters and generate the corresponding stimulation pulses. In some embodiments, the IPG 100 has at least four channels and drives up to sixteen electrodes or more. The electrical circuitry 144 may include additional circuitry such as capacitors, integrated circuits, resistors, coils, and the like configured to perform a variety of functions as best serves a particular application.

In the example illustrated in FIG. 2, the IPG 100 includes two or more leadless electrodes 142. However, either or both of the electrodes 142 may alternatively be located at the ends of short, flexible leads as described in U.S. patent application Ser. No. 09/624,130, filed Jul. 24, 2000, which is incorporated herein by reference in its entirety. The use of such leads permits, among other things, electrical stimulation to be directed to targeted tissue(s) a short distance from the surgical fixation of the bulk of the IPG 100 at a more surgically convenient site. This minimizes the distance traversed and the surgical planes crossed by the IPG 100 and any lead(s).

The external surfaces of the IPG 100 are preferably composed of biocompatible materials. For example, the capsule 202 may be made of glass, ceramic, metal, or any other material that provides a hermetic package that excludes water vapor but permits passage of electromagnetic fields used to transmit data and/or power. The electrodes 142 may be made of a noble or refractory metal or compound, such as platinum, iridium, tantalum, titanium, titanium nitride, niobium or alloys of any of these, to avoid corrosion or electrolysis which could damage the surrounding tissues and the device.

The IPG 100 may also include one or more infusion outlets 201. The infusion outlets 201 facilitate the infusion of one or more drugs into the target tissue. The infusion outlets 201 may dispense one or more drugs directly to the target tissue. Alternatively, catheters may be coupled to the infusion outlets 201 to deliver the drug therapy to target tissue some distance from the body of the IPG 100. If the IPG 100 is configured to provide a drug stimulation using infusion outlets 201, the IPG 100 may also include a pump 149 that is configured to store and dispense the one or more drugs.

Of course, the IPG 100 of FIG. 2 is illustrative of many types of IPGs that may be used to apply electrical stimulation to target tissue to treat a particular medical condition. Other types of IPGs, as well as details concerning IPG manufacture and operation can be found in the various patent documents incorporated by reference elsewhere in this disclosure.

Figure 3:
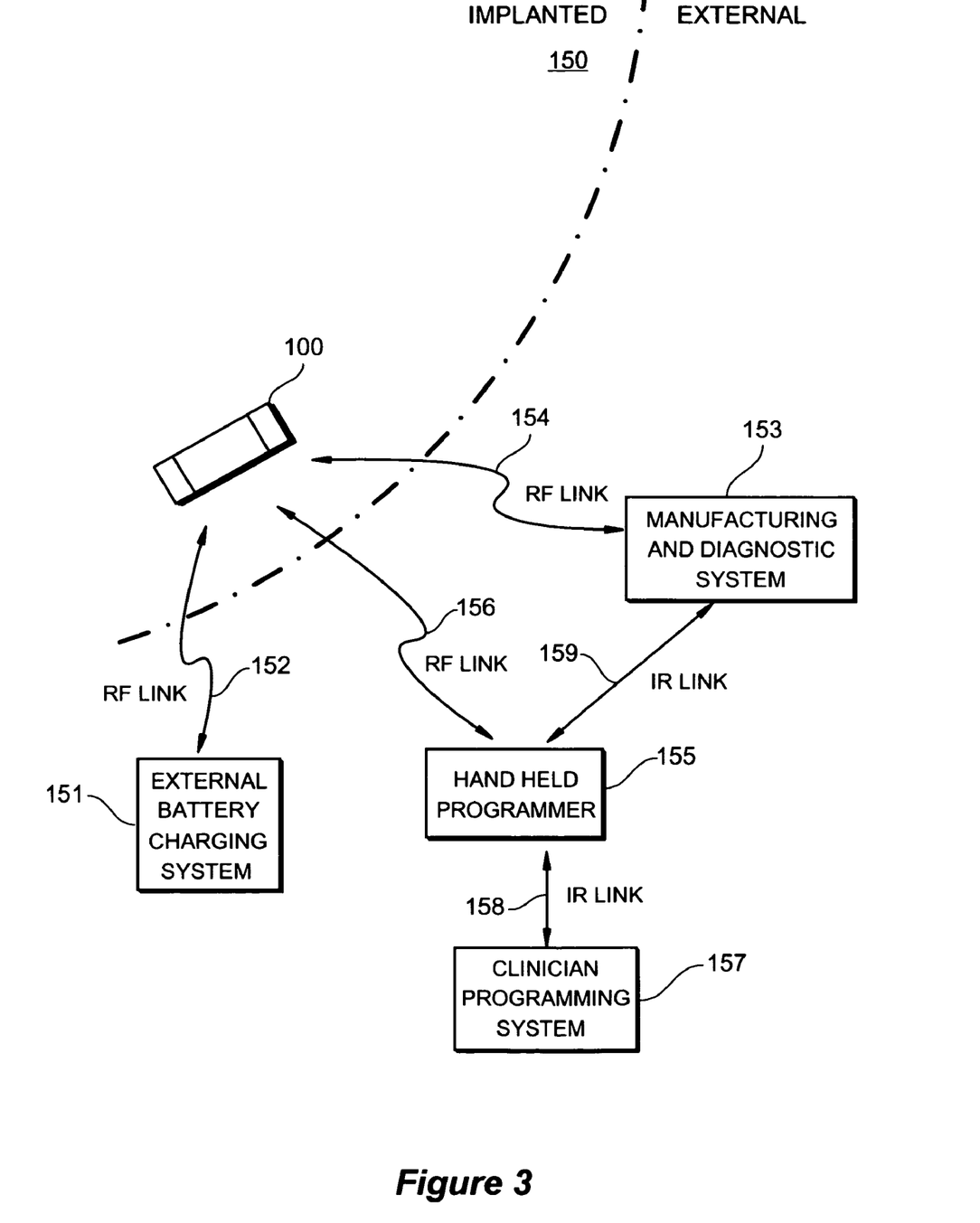
FIG. 3 illustrates the IPG of FIG. 2 and its interaction with various external components in an IPG communication system.

Turning to FIG. 3, the IPG 100 is illustrated as implanted in a patient 150, and further shown are the various external components that may be used to support the implanted IPG 100. For example, an external battery charging system (EBCS) 151 provides power used to recharge the power source (145, FIG. 2) via an RF link 152. As is known in the art, the RF link comprises electromagnetic energy which energizes the coil 147 (FIG. 2) through the patient 150's tissue, and which is rectified, filtered, and sent to recharge the power source 145.

Other external components such as a hand held programmer (HHP) 155, clinician programming system (CPS) 157, and/or a manufacturing and diagnostic system (MDS) 153 preferably activate, deactivate, program, and test the IPG 100 via one or more RF links 154, 156. Thus, one or more of these external devices 153, 155, 157 may also be used to control the IPG 100 to provide stimulation electrical pulses necessary to treat a particular medical condition, and may be used to provide or update the stimulation parameters and other data stored in the programmable memory (146, FIG. 2) of the IPG 100. Furthermore, the external devices 153, 155, 157 may communicate with each other. For example, the CPS 157 may communicate with the HHP 155 via an infrared (IR) link 158 or via any other suitable communication link. Likewise, the MDS 153 may communicate with the HHP 155 via an IR link 159 or via any other suitable communication link.

Additionally, the IPG 100 may report its status or various other parameters to any of the external devices via the two-way RF links 152, 154, and 156. For example, once the logic circuitry detects that the power source 145 is fully charged, the coil 147 (FIG. 2) is used to telemeter that fact back to the EBCS 151 so that charging can cease. Likewise, once stimulation parameters are sent from either of the HHP 155 or the MDS 153, acceptance of those parameters can be telemetered back to those devices, and/or the actual parameters can be telemetered back as a double check.

The HHP 155, MDS 153, CPS 157, and EBCS 151 are merely illustrative of the many different external components that may be used in connection with the IPG 100. Furthermore, it will be recognized that the functions performed by the HHP 155, MDS 153, CPS 157, and EBCS 151 may be performed by a single external device. One or more of these external devices may be embedded in a seat cushion, mattress cover, pillow, garment, belt, strap, pouch, or the like, so as to be conveniently placed near the implanted IPG 100 when in use.

With the following implantable and external components of the system understood, an exemplary method in which the IPG 100 can be used to treat a particular medical condition is briefly illustrated. First, the IPG 100 is implanted so that its electrodes (142, FIG. 2) are coupled to or located near a target tissue. If the IPG 100 is a microstimulator, such as the Bion® microstimulator, the microstimulator itself may be coupled to the target tissue. The IPG 100 is programmed with stimulation parameters to apply at least one stimulus to the target tissue. When the patient desires treatment with the programmed stimulation parameters, the patient sends a command to the IPG 100 (e.g., via a remote control) and the IPG 100 in turn delivers the prescribed stimulation. The IPG 100 may be alternatively or additionally configured to automatically apply the electrical stimulation in response to sensed indicators of the particular medical condition. To cease electrical stimulation, the patient may turn off the IPG 100 (again, via the remote control). When necessary, the EBCS 151 is activated to recharge the power source 145 as described above, and this can occur at convenient intervals for the patient 150, such as every night.

Figure 4:
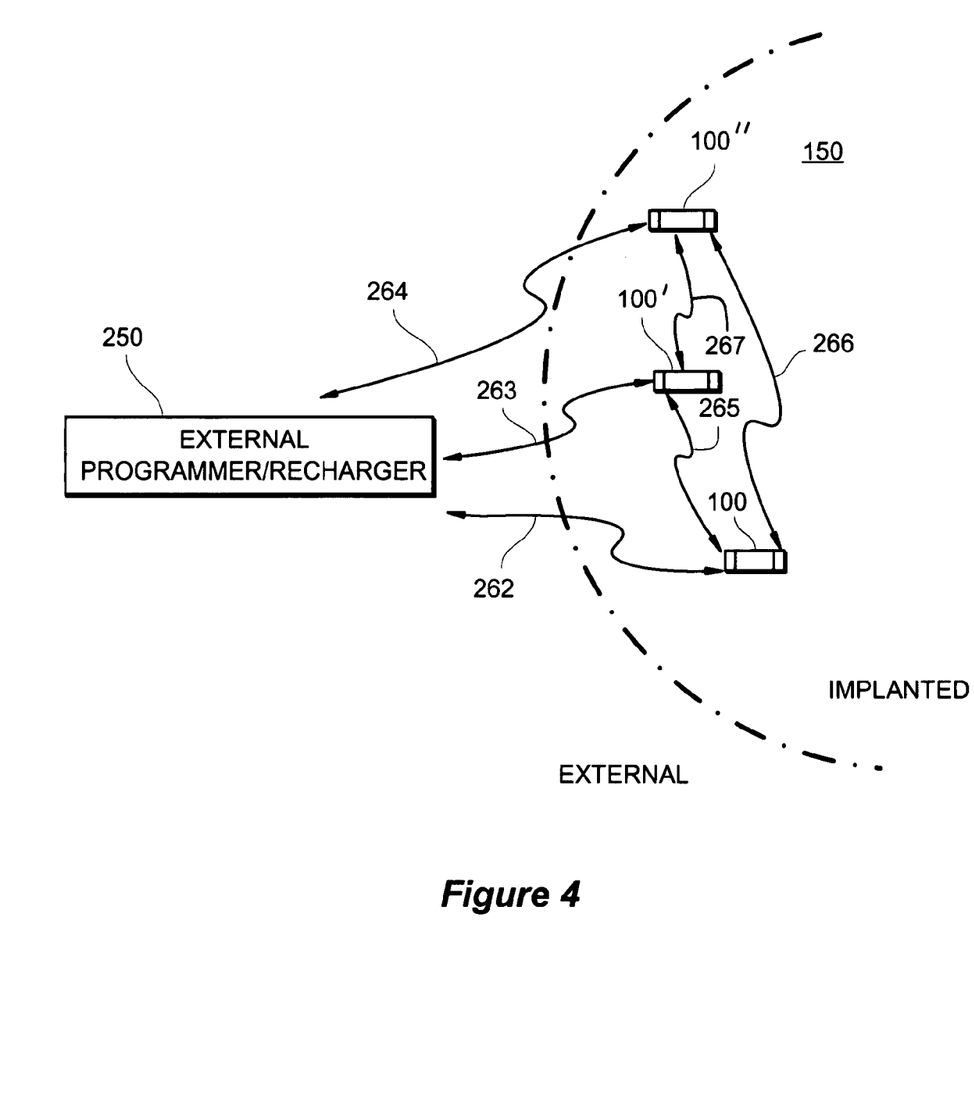
FIG. 4 illustrates several IPGs of FIG. 2 used together in a communication network.

In some therapies, it may be desirable to employ more than one IPG 100, each of which could be separately controlled by means of a telemetered digital address. This allows multiple channels and/or multiple patterns of electrical stimulation to be used as is efficacious for certain medical conditions. For instance, as shown in the example of FIG. 4, a first IPG 100 implanted in a patient 150 provides a stimulus to a first location; a second IPG 100' provides a stimulus to a second location; and a third IPG 100" provides a stimulus to a third location. As mentioned earlier, the implanted devices may operate independently or may operate in a coordinated manner with other implanted devices or other devices external to the patient's body. That is, an external controller 250 (indicative of any of the external components of FIG. 3) may be configured to control the operation of each of the implanted devices 100, 100', and 100" via RF links 262-264. In some embodiments, one implanted device, e.g. IPG 100, may control or operate under the control of another implanted device(s), e.g., IPG 100' and/or IPG 100", via RF links 265-267.

As a further example of multiple IPGs 100 operating in a coordinated manner, the first and second IPGs 100, 100' of FIG. 4 may be configured to sense various indicators of a particular medical condition and to transmit the measured information to the third IPG 100". The third IPG 100" may then use the measured information to adjust its stimulation parameters and to apply modified electrical stimulation to the target tissue accordingly.

Alternatively, the external device 250 may be configured to sense various indicators of a patient's condition. The sensed indicators can then be transmitted to one or more of the implanted IPGs which may adjust stimulation parameters accordingly. In other examples, the external controller 250 may determine whether any change to stimulation parameters is needed based on the sensed indicators. The external device 250 may then signal a command to one or more of the IPGs to adjust stimulation parameters accordingly.

With the basic structure of an implantable stimulator understood, focus now shifts to a detailed description of the DC-to-DC conversion techniques that are the focus of this disclosure.

As noted earlier, the DC-to-DC converter 22 (FIG. 1) boosts the battery voltage, Vbat, to a proper compliance voltage V+ under control of the compliance voltage monitor and adjust circuit 18. However, previous circuitry used to achieve such functionality has been non-optimal, particularly as applied to implantable stimulator devices in which physical space and power are limited. Step-up converters can achieve high voltages with good resolution required for the compliance voltage in an implantable stimulator device application, but suffer in their power efficiency when converting to higher voltages. Moreover, to the extent that the coil in the step up converter is used for other functions in the device, such as telemetry and charging, high voltages placed on the coil by the step-up converter can be deleterious to circuits involved with such other functions. Charge pump circuits are also non-optimal for use as the DC-to-DC converter 22 in an implantable stimulator device due to the difficulty involved in precisely tailoring the output voltage and/or the requirement to use additional off-chip capacitors to solve this precision problem.

Figure 5:
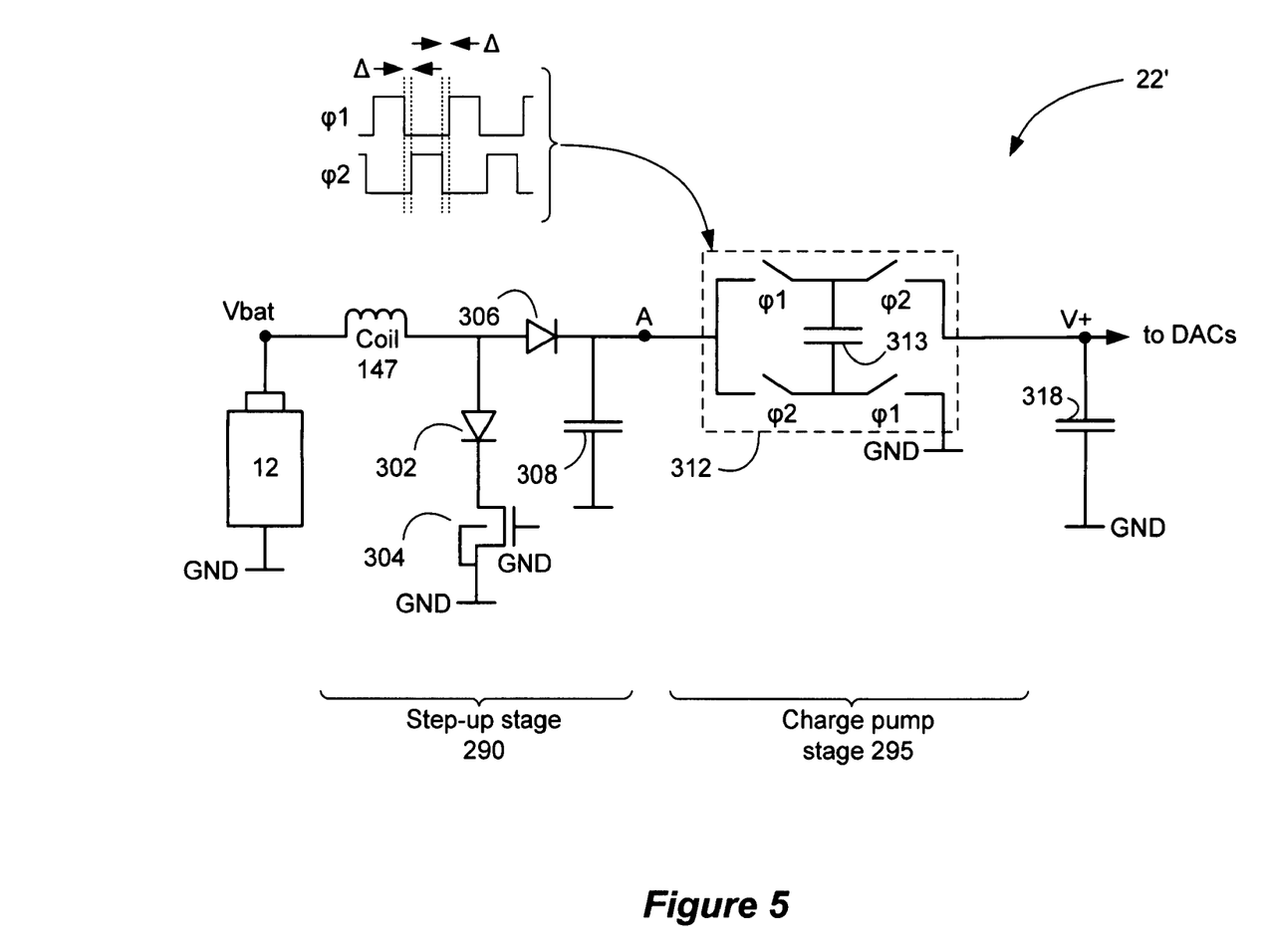
FIG. 5 illustrates an embodiment of the improved DC-to-DC converter circuitry for an IPG in accordance with one embodiment of the invention.

The solution proposed herein is to use a cascaded approach for the DC-to-DC converter 22 which utilizes both of these approaches in series, as shown in basic form in FIG. 5. As shown, the improved DC-to-DC converter 22' uses a first stage 290 comprising a step-up converter. This first stage 290 is used to raise the battery voltage, Vbat, to an intermediate value at node A. Thereafter, the intermediate value A is input to a second stage 295 comprising a charge pump. This second stage 295 is use to raise the intermediate voltage, A, to the final compliance voltage V+ needed by the implantable stimulator device 10 to produce proper stimulating output currents.

Prior to discussing the operation of each of the stages, it can be appreciated that the improved converter circuitry 22' has significant benefits. Suppose the implantable stimulator device 10 requires a very high compliance voltage, V+, of 18 Volts at a particular time. Because of the dual-stage nature of the circuitry 22', the step-up stage 290 is not required to boost the battery voltage Vbat (perhaps 3-4 Volts) to the desired value of 18 Volts. Instead, the step-up stage 290 needs only to boost the voltage to an intermediate value, A, of approximately 9 Volts. At this point, the more-efficient charge pump stage 295 can boost the intermediate voltage A to the desired 18-Volt compliance voltage. Thus, the step-up stage 290 is not hampered by power efficiency problems at high voltages, as it needs only to boost to the lower intermediate voltage. Moreover, this lower intermediate voltage, resulting in approximately half the output voltage, provides an additional circuit design benefit in that the step-up coil 147 can be used for other uses besides voltage conversion without concerns relating to coil overvoltage conditions. Additionally, because the compliance voltage V+ can ultimately be set with good precision by the step-up stage 290, it does not particularly matter that the charge pump 295 lacks such precision. As a result, additional off-chip tuning capacitors are not needed, and space and complexity is thus saved when compared to use of the charge pump stage 295 alone.

With such benefits of the improved circuitry 22' understood, focus now turns to a brief discussion of the operation of each stage 290 and 295. The step up stage 290 employs a coil 147, which as noted earlier is preferably used for other functions in the IPG 100 as well, such as RF telemetry and EM charging. When transistor (switch) 304 is gated on, the coil 147 is grounded, and current flows through the coil and through diode 302. Later, when the switch 304 is turned off, the current in the coil must discharge and does so through diode 306 to charging capacitor 308, whose top plate comprises intermediate node A. Because the capacitor 308 was already charged to the battery voltage, Vbat, the additional charge from the coil boosts the voltage at intermediate node A to a value higher than Vbat. Diode 306 prevent this excess charge from dissipating backwards into the circuit, and the capacitor 308, in addition to storing the charge, also filters to voltage at intermediate node A to stabilize it. Thus, as the gate of switch 304 oscillates between on and off, the voltage at intermediate node A continues to boost. To reduce the voltage at intermediate node A, the oscillations at the gate are halted temporarily, as explained further below with reference to FIG. 6.

The charge pump stage 295 in one embodiment comprises a "doubler" circuit 312, in which the output voltage from the stage is scaled to approximately twice the input to the stage. However, other types of charge pumps could be used to scale to output voltage to different values, or to allow the scalar of the stage to be set to variable values. In the embodiment shown, two clocks, φ1 and φ2, govern the charging of a capacitor 313. The clocks φ1 and φ2, as the timing diagram in FIG. 5 suggests, are essentially 50% duty cycle clocks which are out of phase, although as shown, each of the clocks are off together for a brief period, Δ, to prevent interference between the two clock phases. In operation, during the assertion of φ1, the capacitor 313 is charged to the intermediate voltage A. Then, during the assertion of φ2, the previously-grounded (lower) plate of capacitor 313 is coupled to the intermediate voltage A. Because A was already present on the top plate of the capacitor 313, presenting that same voltage to the bottom plate boosts the voltage on the top plate to roughly 2A. Filtering capacitor 318 helps to stabilize the output voltage (i.e., the compliance voltage V+) produced by the converter 22' on its way to the current sources, i.e., DACs.

Figure 6:
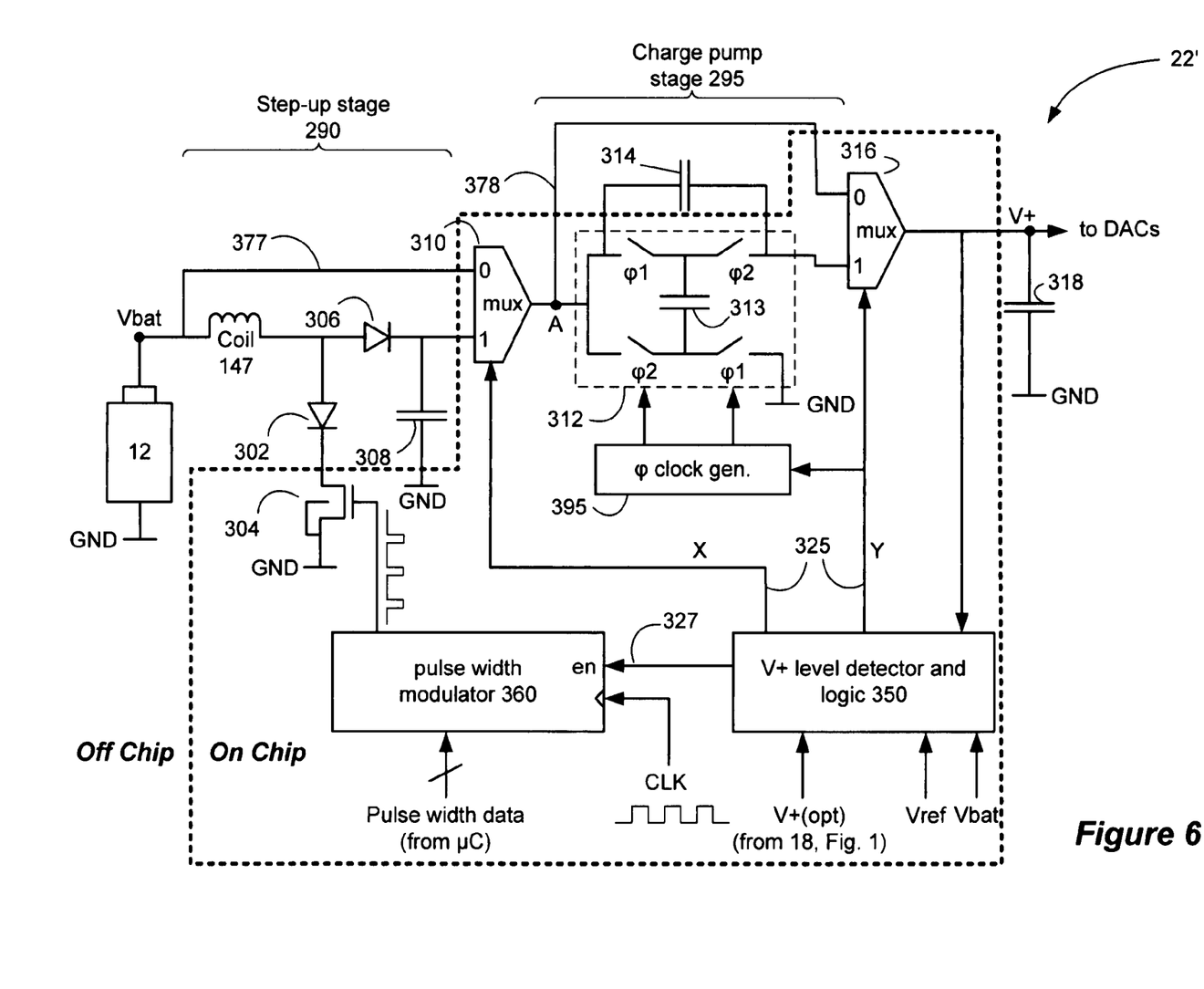
FIG. 6 illustrates further details of the DC-to-DC converter circuitry of FIG. 5, including circuitry to selectively activate the stages of the circuitry.

Further implementation details concerning the improved DC-to-DC converter 22' in an IPG 100 are shown in FIG. 6. Because the improved converter 22' as disclosed herein is used to generate a compliance voltage, V+, additional circuitry relevant to adjustment of the compliance voltage is present, although of course the two-stage converter 22' could be used in other contexts.

Much of the additional circuitry in FIG. 6 exists in recognition that both stages 290, 295 may not always need to be active, and that the desired compliance voltage can dictate which stage(s) is/are active at any given time. Central to such control is the provision of a compliance voltage level detector and logic circuitry 350. As shown, the detector and logic circuit 350 receives the generated compliance voltage, V+, as feedback, and also receives the optimal compliance voltage, V+(opt), from the compliance voltage monitor and adjust circuitry 18 (FIG. 1), as discussed in the Background section of this disclosure.

In any event, level detector and logic circuitry 350 determines V+ by comparison to a stable reference voltage, Vref, which might be generated by a band gap voltage regulator, for instance. Once determined, the compliance voltage V+ is compared against the determined optimal compliance voltage, V+(opt). V+(opt) can be digital in nature, and may be sent to level detector and logic circuit 350 along a digital bus. One skilled in the art will recognize that level detector and logic circuit 350 can be constructed in any number of ways, and hence such details of the circuitry are not disclosed.

After assessing the desired compliance voltage, V+(opt) and the compliance voltage V+ actually produced, circuit 350 generates control signals 325, 327 to control the stages 290, 295 of the improved DC-to-DC converter 22'. Control signal 327 essentially indicates whether the circuit 22' needs to boost the voltage, and specifically indicates the results of a comparison between V+ as generated and the desired V+(opt). If V+ is higher than V+(opt), this indicates that the compliance voltage can be decreased. Accordingly, when this condition is met, control signal 327 disables the pulse width modulator circuit 260 that controls the step-up stage 290. As is well known, a pulse width modulator 360 converts a standard clock signal of a 50% duty cycle (CLK) to a clock with a different duty cycle pursuant to a specified pulse width (sent from the microcontroller). When the pulse width modulator 360 is disabled via control signal 327, the gate of transistor 304 is not pulsed and eventually the intermediate voltage at node A, and ultimately the compliance voltage V+, will start to fall. If V+ falls to a level below V+(opt), by contrast, the comparison of these voltages at level detector and logic 350 yields an enabled control signal at 327, which in turn allows the width-modulated pulses to be presented to the gate of transistor 304. Such pulsing, as noted earlier, boosts the voltage at node A, and ultimately V+, to its proper levels.

Control signals 325 are similarly involved in selective activation of the boost stages 290, and 295, with control signal X controlling activation of the step-up stage 290, and control signal Y controlling activation of the charge pump stage 295. Essentially, the control signals 325 reflect the magnitude of V+, and accordingly enable or disable one or both of the stages 290 and 295 in a logical manner depending on that magnitude. For example, if V+ is sufficiently low, there may be no need to boost the battery voltage, Vbat, at all, and instead Vbat may simply be passed directly through as the compliance voltage without boosting at either stage 290, 295. By contrast, if V+ is very high, both stages 290, 295 would be need to be active to derive that voltage from Vbat.

Figure 7:
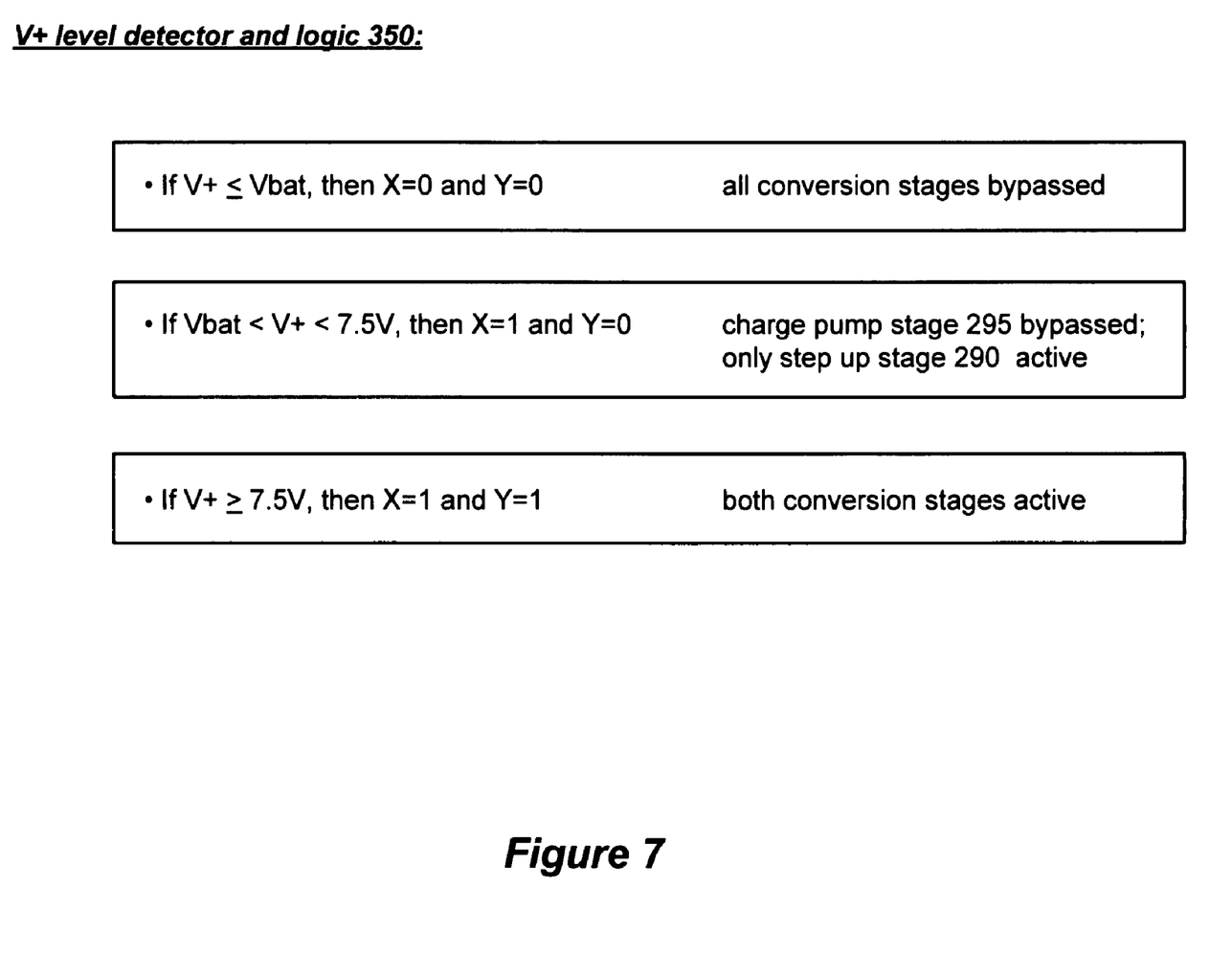
FIG. 7 illustrates conditions pursuant to which the stages of the DC-to-DC converter circuitry of FIG. 5 are selectively activated.

Such selective activation of the stages 290, 295 is exemplified in one embodiment with reference to FIG. 7, which describes the functionality of level detector and logic circuit 350 and the generation of control signals 325. As shown, logic 350, as well as determining V+, compares that voltage to various thresholds to decide which if any of the stages 290 should be activated at a given time. Thus, if V+ is less than or equal to Vbat, controls signals 325, both X and Y, are set equal to zero. Referring again to FIG. 6, it is seen that when X=Y=0, multiplexers 310 and 316 choose to pass their top-most inputs, i.e., paths 377 and 378. Paths 377 and 378 bypass the stages 290 and 295, such that path 377 passes the battery voltage, Vbat, to the intermediary node A, and path 378 passes the intermediary voltage A to the compliance voltage V+. Additionally, with control signal Y=0, the clock generator 395 that generates the charge pump clocking signals φ1 and φ2 is disabled as there is no need for the bypassed charge pump circuit 312 to operate and draw power. In other words, when V+ is less than Vbat, Vbat is simply bypassed to the compliance voltage V+ without boosting from either stage 290, 295. This may not be optimal from a power standpoint, as the compliance voltage would be set to a higher value (Vbat) that is needed. But at low voltage levels, such inefficiency is tolerable.

Referring again to FIG. 7, when V+ is higher than the battery voltage, but below a threshold voltage, for example 7.5 Volts, then control signals 325 are set by logic 350 to X=1 and Y=0. This causes multiplexer 310 to pass the boosted output of the step-up stage 290 at its bottom input, and causes multiplexer 316 to bypass the charge pump stage 295 by passing the intermediate voltage A along path 378 to the compliance voltage output, V+. In other words, the step-up stage 290 is activated, but the charge pump stage 290 is bypassed. Because only a moderate amount of boosting of the battery voltage is required (i.e., up to 7.5V), it is unnecessary to use the charge pump stage 295 to provide the required compliance voltage V+. Moreover, at such moderate boost voltages, problems mentioned earlier associated with step-up converters—power efficiency losses at high voltages and high coil voltages—are less significant and are tolerable. The threshold of 7.5 Volts is somewhat arbitrary and subject to a designer's preference, but preferably constitutes a level at which power efficiency and/or coil voltage become intolerable design constraints.

When V+ is higher than the threshold (e.g., 7.5V), then logic 350 sets control signals 325 to X=1 and Y=1, thus activating both stages 290, 295 to participate in boosting the battery voltage to the required compliance voltage. As noted earlier, by cascading the stages 290, 295 in this manner, high efficiency and precision can be realized in the generation of the compliance voltage.

Although as described above the level detector and logic 350 compares the battery voltage and threshold to the actually-produced compliance voltage, V+, it should be noted that the same comparison and generation of the control signals 325 can be made with reference to the optimal compliance voltage, V+(opt) as well.

With the functionality of the circuitry thus explained, it should be appreciated that implementation of the various circuit blocks would be well within the knowledge of one skilled in the art, and could be implemented in any number of different ways.

As shown in FIG. 6, much of the improved DC-to-DC converter 22' is preferably implemented in an integrated circuit. Such an integrated circuit in the IPG 100 would typically comprise other circuits, such as the DACs, etc., but are not shown in the Figures for simplicity. Other "off-chip" discrete components, such as the various capacitors, coil 147, battery 12, etc., will couple to the integrated circuit via a printed circuit board positioned in the capsule 200 of the IPG 100, as is well known.

While the improved DC-to-DC converter 22' comprises two boosting stages, it should be appreciated that more than two stages could also be used. For example, two series-connected charge pump stages 295 can be used on the output to supplement the step-up converter used at the input. Moreover, and as noted earlier, different types of boosting circuitry can be used beyond the step-up converter and charge pumps disclosed herein, and different circuitry configurations can be used for both step-up converter and charge pumps compared to the circuit implementations disclosed herein. Additionally, it should be noted that while it is preferred that the step-up stage 290 precede the charge pump stage 295, this is not required. Instead, the two stages could be serially connected in the opposite order, with many of the same benefits as disclosed herein.

A "boosting stage" as used herein should be understood as a circuit capable, when activated, of boosting a DC input voltage to a higher DC output voltage. So understood, it should be appreciated that two boosting stages in series can comprise a single "boosting stage." For example, two serially connected charge pumps can be viewed as a single "boosting stage," even if between them they generate an intermediate voltage. "Bypassing" a boosting stage should be understood as passing its input to its output without boosting.

While the invention herein disclosed has been described by means of specific embodiments and applications thereof, numerous modifications and variations could be made thereto by those skilled in the art without departing from the literal and equivalent scope of the invention set forth in the claims.

What is claimed is:

1. A method for boosting a battery voltage to a compliance voltage in an implantable medical device, comprising:
   boosting a battery voltage to an intermediate voltage using at least a first boosting stage;
   if a compliance voltage is higher than a threshold voltage, boosting the intermediate voltage to the compliance voltage using at least a second boosting stage, else using the intermediate voltage as the compliance voltage; and
   using the compliance voltage to drive a current through an electrode of the implantable medical device for stimulating a patient's tissue.

2. The method of claim 1, wherein the first boosting stage comprises a switched LC circuit, and wherein the second boosting stage comprises a doubler.

3. The method of claim 1, wherein the first boosting stage comprises a step-up converter, and wherein the second boosting stage comprises a charge pump.

4. The method of claim 1, wherein one of the first or second boosting stages comprises a step-up converter, and wherein the other comprises a charge pump.

5. A method for boosting a battery voltage to a compliance voltage in an implantable medical device, the device comprising a battery voltage coupled to at least a first boosting stage for producing a first voltage, and the first voltage coupled to at least a second boosting stage for producing a compliance voltage, comprising:
   using the compliance voltage to drive a current through an electrode of the implantable medical device for stimulating a patient's tissue;
   assessing the magnitude of the compliance voltage;
   depending on the magnitude of the compliance voltage, generating control signals; and
   selectively activating none, some, or all of the boosting stages in accordance with the control signals, wherein failure to activate a boosting stage comprises bypassing that boosting stage.

6. The method of claim 5, wherein the first boosting stage comprises a different circuit than the second boosting stage.

7. The method of claim 5, wherein one of the first or second boosting stages comprises a step-up converter, and wherein the other comprises a charge pump.

8. The method of claim 7, wherein the step-up converter comprises a switched LC circuit, and wherein the charge pump comprises a doubler.

9. The method of claim 5, wherein bypassing a boosting stage comprises use of a multiplexer.

10. The method of claim 5, wherein assessing the magnitude of the compliance voltage comprises determining if the compliance voltage is less than or equal to the battery voltage, and if so, activating none of the boosting stages in accordance with the control signals.

11. The method of claim 5, wherein assessing the magnitude of the compliance voltage comprises comparing the compliance voltage against a threshold, and if the compliance voltage is less than a threshold, activating only some of the boosting stages in accordance with the control signals.

12. The method of claim 11, wherein if the compliance voltage is greater than or equal to the threshold, activating all of the boosting stages in accordance with the control signals.

13. Circuitry for an implantable medical device, comprising:
a battery having a battery voltage;
a step-up converter, wherein the step-up converter receives the battery voltage at its input and is selectable to produce an intermediate voltage higher than the battery voltage at its output;
a charge pump, wherein the charge pump receives the intermediate voltage at its input and is selectable to produce a compliance voltage higher than the intermediate voltage at its output;
control logic for selectively activating the step-up converter and for selectively activating the charge pump in accordance with a magnitude of the compliance voltage; and
a current source powered by the compliance voltage, configured to provide a predetermined current through an electrode of the implantable medical device for stimulating a patient's tissue.

14. The circuitry of claim 13, wherein the control logic compares the magnitude of the compliance voltage to at least one threshold, and depending on the comparison, selectively activates none, some, or all of the step-up converter and the charge pump.

15. The circuit of claim 14, wherein the control logic activates only one of the step-up converter or the charge pump if the magnitude of the compliance voltage is less than the threshold, and wherein the control logic activates both the step-up converter and the charge pump if the magnitude of the compliance voltage is greater than the threshold.

16. Circuitry for an implantable medical device, comprising:
a battery having a battery voltage;
a first boosting stage, wherein first boosting stage receives the battery voltage at its input and is configured to produce a first output voltage higher than the battery voltage;
a first multiplexer for selecting either the first output voltage or the battery voltage as an intermediate voltage;
a second boosting stage, wherein the second boosting stage receives the intermediate voltage at its input and is configured to produce a second output voltage higher than the intermediate voltage; and
a second multiplexer for selecting either the second output voltage or the intermediate voltage as a compliance voltage,
wherein the compliance voltage provides the power for providing a current through an electrode of the implantable medical device for stimulating a patient's tissue.

17. The circuitry of claim 16, wherein the first boosting stage comprises a switched LC circuit, and wherein the second boosting stage comprises a doubler.

18. The circuitry of claim 16, wherein the first boosting stage comprises a step-up converter, and wherein the second boosting stage comprises a charge pump.

19. The circuitry of claim 16, wherein one of the first or second boosting stages comprises a step-up converter, and wherein the other comprises a charge pump.

20. The circuitry of claim 16, wherein the first boosting stage comprises a different circuit than the second boosting stage.

21. The circuitry of claim 16, wherein the first multiplexer is controlled by a first control signal to select the intermediate voltage, and wherein the second multiplexer is controlled by a second control signal to select the compliance voltage.

22. The circuitry of claim 21, wherein the first and second control signals are generated dependent upon a magnitude of the compliance voltage.

23. Circuitry for an implantable medical device, comprising:
a battery having a battery voltage;
a first boosting stage, wherein first boosting stage receives the battery voltage at its input and is configured to produce an intermediate voltage;
a second boosting stage, wherein the second boosting stage receives the intermediate voltage at its input and is configured to produce an output voltage higher than the intermediate voltage; and
a multiplexer for selecting in accordance with a control signal either the output voltage or the intermediate voltage as an actual compliance voltage,
wherein the actual compliance voltage provides the power for providing a current through an electrode of the implantable medical device for stimulating a patient's tissue.

24. The circuitry of claim 23, wherein the first boosting stage comprises a step-up converter, and wherein the second boosting stage comprises a charge pump.

25. The circuitry of claim 23, wherein one of the first or second boosting stages comprises a step-up converter, and wherein the other comprises a charge pump.

26. The circuitry of claim 23, wherein the first boosting stage comprises a different circuit than the second boosting stage.

27. The circuitry of claim 23, wherein the control signal controls the multiplexer to select the output voltage when the compliance voltage is above a threshold voltage, and wherein the control signal controls the multiplexer to select the intermediate voltage when the compliance voltage is below the threshold voltage.

28. The circuitry of claim 23, wherein the control signal activates the second boosting stage to produce the output voltage.

29. The circuitry of claim 23, wherein the first boosting stage is activated to produce the intermediate voltage when the actual compliance voltage is less than an optimal compliance voltage.

* * * * *